(12) United States Patent
Nagata

(10) Patent No.: US 10,058,378 B2
(45) Date of Patent: Aug. 28, 2018

(54) TREATMENT TOOL

(71) Applicant: OLYMPUS CORPORATION, Hachioji-shi, Tokyo (JP)

(72) Inventor: Takashi Nagata, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/599,796

(22) Filed: May 19, 2017

(65) Prior Publication Data

US 2017/0252098 A1   Sep. 7, 2017

Related U.S. Application Data

(63) Continuation of application No. PCT/JP2016/062018, filed on Apr. 14, 2016.

(30) Foreign Application Priority Data

Apr. 30, 2015   (JP) .................. 2015-093391

(51) Int. Cl.
| | | |
|---|---|---|
| *A61B 18/14* | (2006.01) | |
| *A61B 17/32* | (2006.01) | |
| *A61B 18/00* | (2006.01) | |

(52) U.S. Cl.
CPC .......... *A61B 18/1447* (2013.01); *A61B 17/32* (2013.01); *A61B 18/1442* (2013.01);
(Continued)

(58) Field of Classification Search
CPC .................................................. A61B 18/085
See application file for complete search history.

(56) References Cited

U.S. PATENT DOCUMENTS

| | | | |
|---|---|---|---|
| 5,334,198 A * | 8/1994 | Hart | A61B 17/0467 606/49 |
| 5,573,534 A * | 11/1996 | Stone | A61B 18/1442 606/48 |
| 2008/0297287 A1* | 12/2008 | Shachar | A61B 5/06 335/234 |

FOREIGN PATENT DOCUMENTS

| | | |
|---|---|---|
| JP | 2001-353165 A | 12/2001 |
| JP | 2003-235865 A | 8/2003 |
| WO | 2013/190937 A1 | 12/2013 |

OTHER PUBLICATIONS

Jul. 5, 2016 Search Report issued in International Patent Application No. PCT/JP2016/062018.

(Continued)

*Primary Examiner* — Linda Dvorak
*Assistant Examiner* — Ryan T Clark
(74) *Attorney, Agent, or Firm* — Oliff PLC

(57) ABSTRACT

A treatment tool includes a first gripping member, a second gripping member configured to be opened and closed with respect to the first gripping member, a heat radiating member and a first heat conductive member. A predetermined position between a closed state and an opened state is defined as a switching position in a process of changing the closed state to the opened state, a first region is defined as a region from the closed state to the switching position, and a second region is defined as a region from the switching position to the opened state. The first heat conductive member brings the first gripping member and the heat radiating member into a non-thermally contacted state in the first region, and brings the first gripping member and the heat radiating member into a thermally contacted state in the second region.

11 Claims, 5 Drawing Sheets

(52) U.S. Cl.
CPC ............... *A61B 2018/00589* (2013.01); *A61B 2018/00595* (2013.01)

(56) References Cited

OTHER PUBLICATIONS

Nov. 9, 2017 International Preliminary Report on Patentabililty issued in International Patent Application No. PCT/JP2016/062018.

* cited by examiner

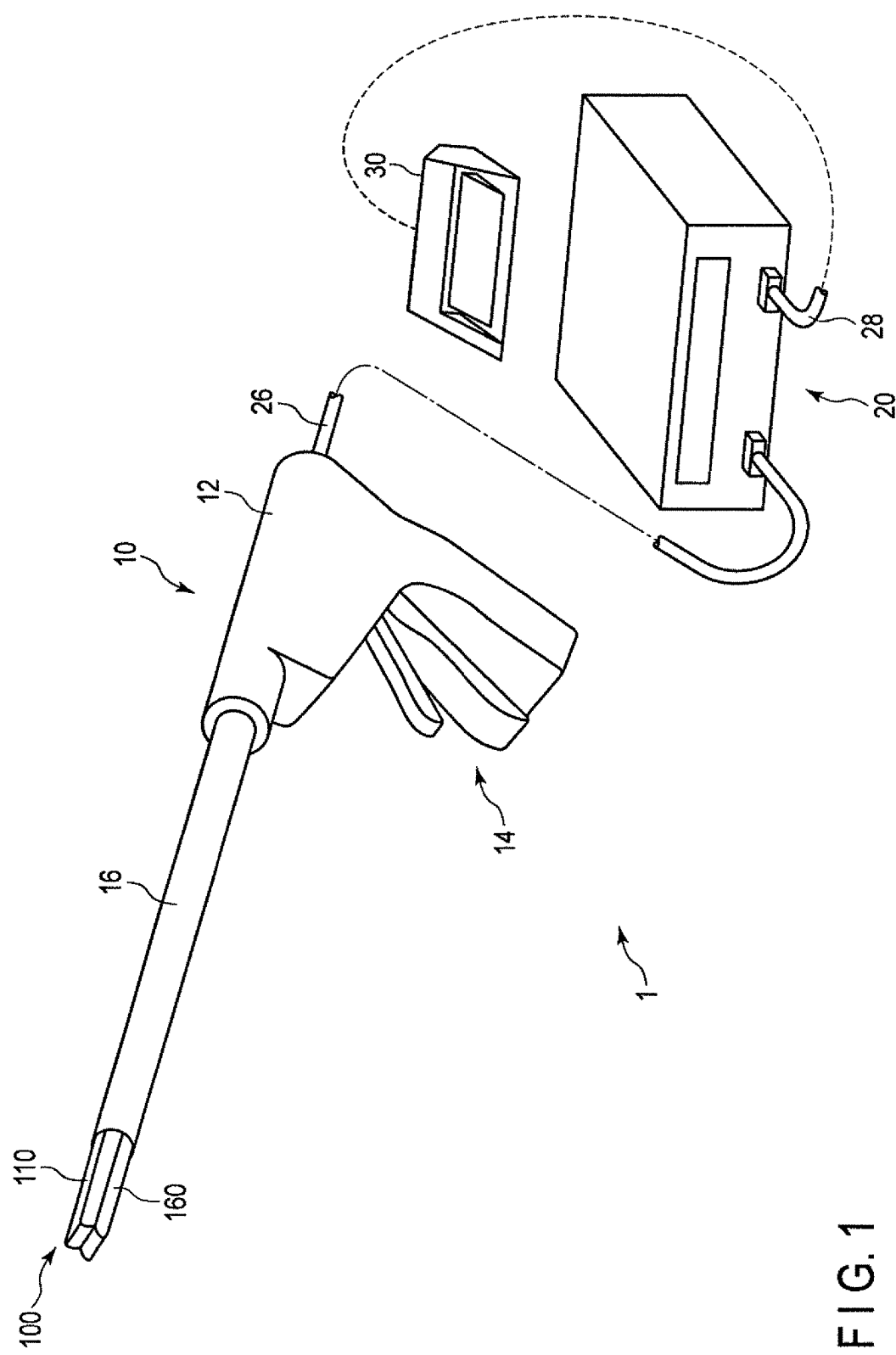
F I G. 1

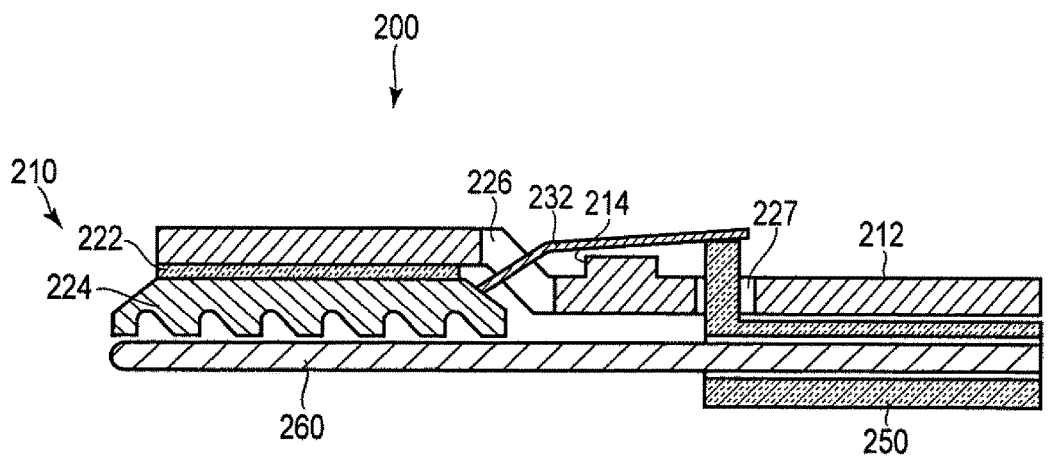
F I G. 4
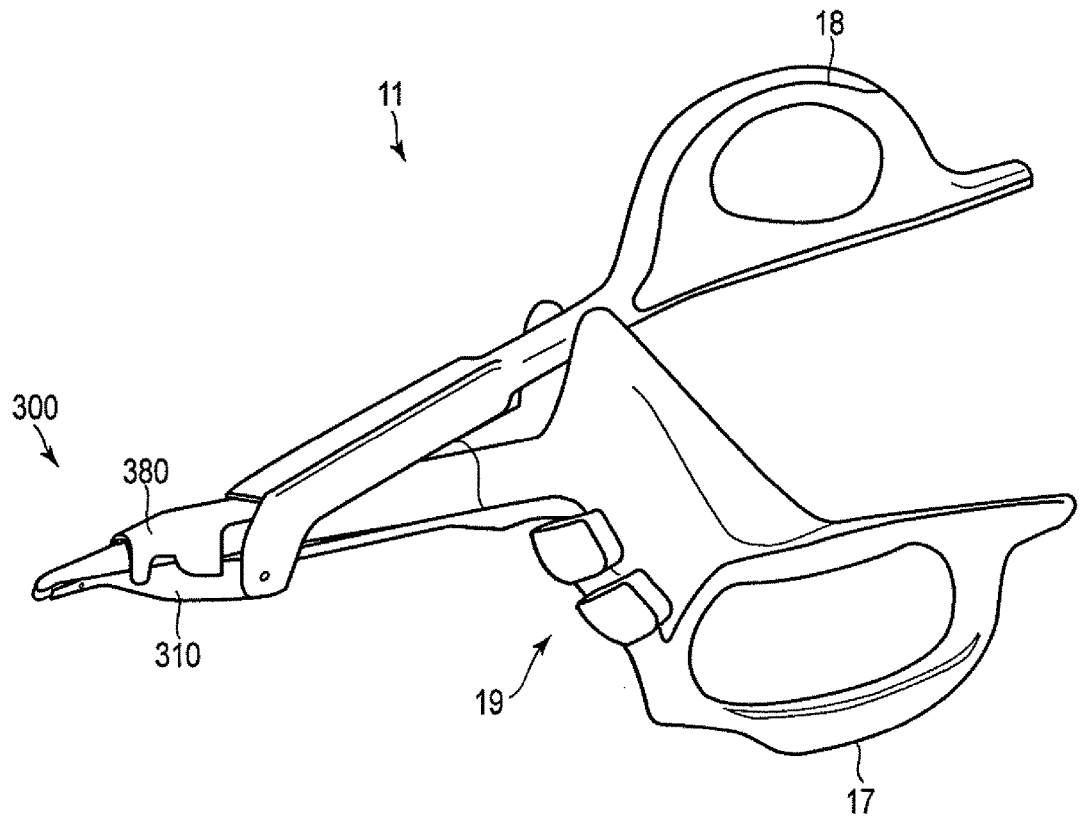
F I G. 5

TREATMENT TOOL

CROSS-REFERENCE TO RELATED APPLICATIONS

This application is a Continuation application of PCT Application No. PCT/JP2016/062018, filed Apr. 14, 2016 and based upon and claiming the benefit of priority from prior Japanese Patent Application No. 2015-093391, filed Apr. 30, 2015, the entire contents of all of which are incorporated herein by reference.

BACKGROUND OF THE INVENTION

1. Field of the Invention

The present invention relates to a treatment tool.

2. Description of the Related Art

A treatment tool that performs treatment on living tissue as a target for treatment using heat is known. Such a treatment tool is used to coagulate, cauterize, or dissect living tissue. With such a treatment tool, various types of energy, such as high-frequency electric power, ultrasonic vibration, and heat generated by a heater, etc., may be used to heat living tissue. In any case, it is required to keep a portion which is in contact with living tissue at a high temperature during treatment, whereas immediate cooling of the portion is required when treatment is not performed.

Jpn. Pat. Appln. KOKAI Publication No. 2001-353165, for example, discloses a technique related to a treatment tool in which heat of jaws is transferred when the back of the jaws is in partial contact with a portion of a sheath when the jaws that grip living tissue as a treatment target are completely opened, and the heat is radiated from the sheath.

BRIEF SUMMARY OF THE INVENTION

According to one aspect of the present invention, a treatment tool includes a first gripping member; a second gripping member configured to be opened and closed with respect to the first gripping member; a heat radiating member; and a first heat conductive member that brings the first gripping member and the heat radiating member into a non-thermally contacted state in a first region, and brings the first gripping member and the heat radiating member into a thermally contacted state in a second region, a predetermined position between a closed state in which the first gripping member and the second gripping member are closed and an opened state in which the first gripping member and the second gripping member are opened being defined as a switching position in a process of changing the closed state to the opened state, the first region being defined as a region from the closed state to the switching position, and the second region being defined as a region from the switching position to the opened state.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing an outline of a configuration example of a treatment system according to a first embodiment.

FIG. 4 is a cross-sectional view showing an outline of the configuration example of a gripping section according to an modification of the first embodiment.

FIG. 5 is a perspective view showing an outline of a configuration example of a treatment tool according to a second embodiment.

DETAILED DESCRIPTION OF THE INVENTION

First Embodiment

Figure 2:
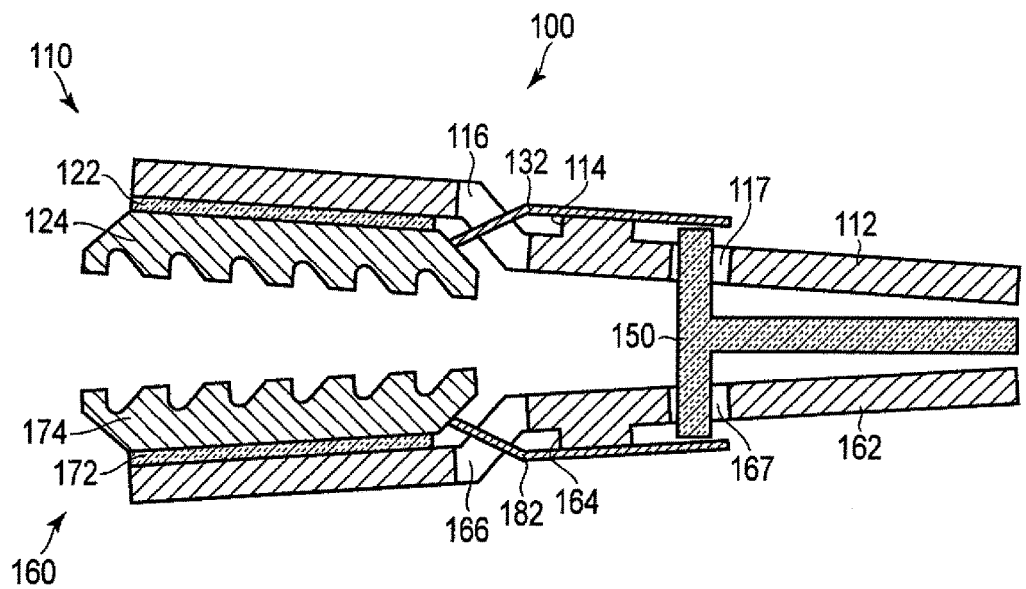
FIG. 2 is a cross-sectional view showing an outline of a configuration example of a gripping section according to the first embodiment, and showing an opened state of the gripping section.

The first embodiment of the present invention will be described with reference to the drawings. FIG. 1 is a diagram showing an outline of a configuration example of a treatment system 1 according to the first embodiment. The treatment system 1 comprises a treatment tool 10, a control device 20, and a foot switch 30. The treatment system 1 is used for treatment in which the treatment tool 10 grips living tissue as a target for treatment, and a high-frequency current that is output from the control device 20 is applied to the living tissue to heat the living tissue.

The treatment tool 10 includes a handle 12, an operation knob 14, a shaft 16, and a gripping section 100. The side where the handle 12 is located is called the proximal side, and the side where the gripping section 100 is located is called the distal side. As shown in FIG. 1, the shaft 16 is connected to the distal side of the handle 12, and the gripping section 100 is provided on the distal portion of the shaft 16.

The gripping section 100 includes a first jaw 110 and a second jaw 160. The first jaw 110 and the second jaw 160 change their positions with respect to each other. The gripping section 100 grips living tissue as a target for treatment by the first jaw 110 and the second jaw 160. An electrode is provided in each of the first jaw 110 and the second jaw 160, as will be described later, to apply a high-frequency voltage to the gripped living tissue.

The handle 12 is a portion at which an operator grips the treatment tool 10. The operation knob 14 changes its position with respect to the handle 12. In synchronization with the position change of the operation knob 14, the space between the first jaw 110 and the second jaw 160 of the gripping section 100 is opened and closed. The shaft 16 is a shaft that connects the gripping section 100 and the handle 12.

The treatment tool 10 is connected to the control device 20 via a first cable 26. The control device 20 is connected to the foot switch 30 via a second cable 28. The control device 20 detects the foot switch 30 being on/off, and outputs high-frequency electric power to the treatment tool 10 in accordance with the foot switch being on/off. The switch for switching the output may be a switch provided in the treatment tool 10, not a foot switch. The control device 20 adjusts electric power supplied to the treatment tool 10 by a feedback control to maintain the power at a power preset by the operator, for example.

Next, the operation of the treatment system 1 according to the present embodiment is described. The operator operates an input section of the control device 20 to set an output condition for the treatment tool 10, for example an output level of frequency energy, etc. The gripping section 100 and the shaft 16 of the treatment tool 10 are inserted into, for example, an abdominal cavity through an abdominal wall.

The operator closes/opens the gripping section 100 by operating the operation knob 14 to grip living tissue as a target for treatment by the first jaw 110 and the second jaw 160. Upon gripping living tissue as a target for treatment by the gripping section 100, the operator operates the foot switch 30. When the foot switch 30 is switched on, electric power is supplied to the treatment tool 10 from the control device 20 via the first cable 26. As a result, a high-frequency voltage is applied between the first jaw 110 and the second jaw 160, and a high-frequency current flows in the living tissue. This high-frequency current causes the living tissue to generate heat and to be, for example, coagulated, cauterized, or dissected. The treatment of living tissue is thus completed.

Figure 3:
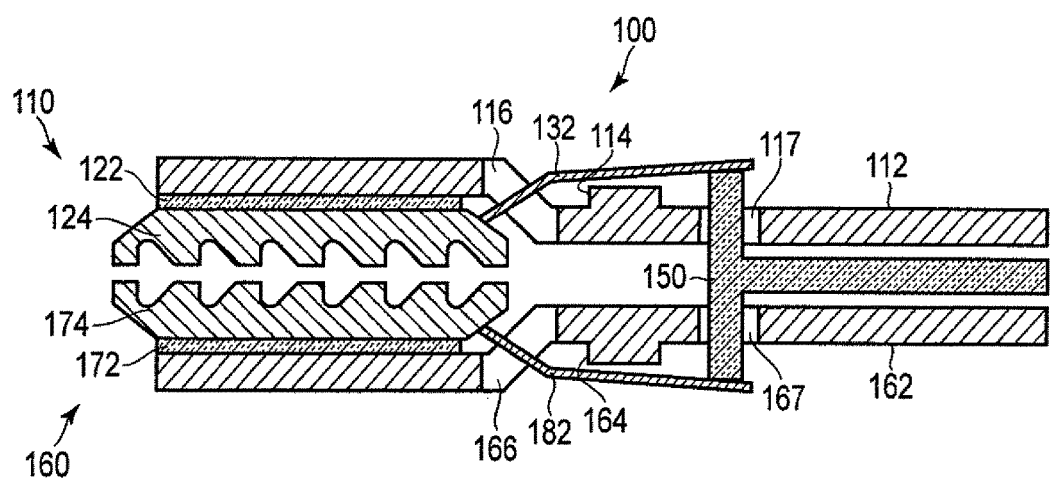
FIG. 3 is a cross-sectional view showing an outline of a configuration example of the gripping section according to the first embodiment, and showing a closed state of the gripping section.

The configuration example of the gripping section 100 will be explained with reference to FIG. 2 to FIG. 3. FIG. 2 is a cross-sectional diagram of the gripping section 100, illustrating the opened state of the gripping section 100. FIG. 3 is a cross-sectional diagram of the gripping section 100, illustrating the closed state of the gripping section 100. In the present embodiment, the first jaw 110 and the second jaw 160 which constitute the gripping section 100 have a symmetrical structure.

The first jaw 110 has a first jaw main body 112. The first jaw main body 112 is made of a material having a good heat conductivity, for example a metal. The first jaw main body 112 is connected to the distal portion of the shaft 16 in such a manner that the angle with respect to the shaft 16 changes. The side of the first jaw main body 112 that faces the second jaw 160 is called the inner side, and the other side is called the outer side.

A first distal gripping member 124 is provided on the surface of the distal portion of the first jaw main body 112 that faces the second jaw 160, i.e., the inner side of the distal portion of the first jaw main body 112, with a first heat insulating member 122 being interposed therebetween. The first distal gripping member 124 is made of a metal, etc. having a good electric conductivity. The first distal gripping member 124 is designed to be in contact with living tissue as a target for treatment. Herein, the first distal gripping member 124 functions as an electrode that applies a voltage to living tissue. Accordingly, the first distal gripping member 124 is connected to a non-illustrated lead wire for supplying a high-frequency current that is output from the control device 20 to the first distal gripping member 124. The electric power may be supplied to the first distal gripping member 124 via the first jaw main body 112.

When treatment is performed on living tissue, the first jaw 110 and the second jaw 160 are closed as shown in FIG. 3. A second distal gripping member 174, which will be described later, is provided at the second jaw 160 so as to be symmetrical with the first distal gripping member 124. When the first jaw 110 and the second jaw 160 are closed, the first distal gripping member 124 and the second distal gripping member 174 are in contact with living tissue. In this case, a high-frequency voltage is applied between the first distal gripping member 124 and the second distal gripping member 174, and a high-frequency current flows in the living tissue. As a result, the living tissue generates heat, and treatment, such as cauterization and dissection, is performed. When treatment is performed while a voltage is being applied to living tissue, the first distal gripping member 124 and the second distal gripping member 174 also become hot.

The first heat insulating member 122 is a member provided to prevent heat of the first distal gripping member 124 from being transferred to the first jaw main body 112. The first heat insulating member 122 is made of a publicly-known material with a low heat conductivity, such as a resin, glass fibers, ceramics, etc. The first heat insulating member 122 may be of a shape having a space for heat insulation.

Since the high-frequency electric power supplied to the first distal gripping member 124 is a large electric power, the lead wire for supplying electric power to the first distal gripping member 124 needs to be as thick as possible to withstand the supplied electric power. On the other hand, the heat of the first distal gripping member 124 can be transferred to this lead wire. Accordingly, it is preferable that the lead wire preferably has a sufficient thickness to withstand the large electric power that is supplied and is to be as thin as possible to make the transmission of the heat from the first distal gripping member 124 difficult.

In the first jaw main body 112, a first hole 116 through which an after-described first heat conductive member 132 penetrates is provided to a proximal side of the position where the first heat insulating member 122 is provided. In the first jaw main body 112, a first projecting portion 114, which serves as a portion in contact with the first heat conductive member 132, is provided to a proximal side of the first hole 116. In the first jaw main body 112, a second hole 117 into which an after-described forcing member 150 penetrates is provided to a proximal side of the first projecting portion 114.

A first heat conductive member 132 is connected to the first distal gripping member 124. The first heat conductive member 132 is made of a material, such as a metal, etc. having good heat conductivity. The first heat conductive member 132 has elasticity. In other words, the first heat conductive member 132 includes an elastic member having heat transfer capabilities. The first heat conductive member 132 extends from the first distal gripping member 124 provided on the inner side of the first jaw main body 112 through the first hole 116 provided in the first jaw main body 112 to the outside of the first jaw main body 112. This first heat conductive member 132 extends from the distal end where the first distal gripping member 124 is provided toward the proximal side, up to a portion where the second hole 117 is provided.

In the present embodiment, the first jaw 110 and the second jaw 160 constitute a symmetrical structure. In other words, the second jaw 160 has a second jaw main body 162 corresponding to the first jaw main body 112. A second projecting portion 164 corresponding to the first projecting portion 114 in the first jaw main body 112 is provided in the second jaw main body 162. A third hole 166 and a fourth hole 167 respectively corresponding to the first hole 116 and the second hole 117 of the first jaw main body 112 are provided in the second jaw main body 162. A second heat insulating member 172, a second distal gripping member 174, and a second heat conductive member 182 respectively corresponding to the first heat insulating member 122, the first distal gripping member 124, and the first heat conductive member 132 are further provided in the second jaw 160.

The gripping section 100 has a forcing member 150. The forcing member 150 is made of a material having heat insulation properties. The forcing member 150 is fixed with respect to the shaft 16, and extends from the inner side, which is a space where the first jaw main body 112 and the second jaw main body 162 face each other, through the second hole 117 to the outside of the first jaw main body 112, i.e., to the proximity of the first heat conductive member 132, and also extends through the fourth hole 167 to the outside of the second jaw main body 162, i.e., to the proximity of the second heat conductive member 182.

Next, the mechanism of the gripping section 100 will be explained with reference to FIG. 2 and FIG. 3.

When the gripping section 100 is opened, the first heat conductive member 132 is in contact with the first projecting portion 114 of the first jaw main body 112, as shown in FIG. 2. Accordingly, the heat of the first distal gripping member 124 is transferred to the first jaw main body 112 via the first heat conductive member 132. Since the first jaw main body 112 has a large volume, its heat capacity is large. Furthermore, since the first jaw main body 112 has a high heat conductivity and a large surface area, heat tends to be easily radiated from the first jaw main body 112.

As the gripping section 100 is gradually closed, the first heat conductive member 132 is in contact with the forcing member 150. A position of the first jaw 110 and the second jaw 160, where the state is switched from a state in which the first heat conductive member 132 is not in contact with the forcing member 150 to a state in which they are in contact with each other, will be called a switching position. If the gripping section 100 is further closed after the switching position, since the first heat conductive member 132 has elasticity, the first heat conductive member 132 is deformed while in contact with the forcing member 150. By this deformation, the first heat conductive member 132 is no longer in contact with the first projecting portion 114. The completely-closed state of the gripping section 100 is similar to the state shown in FIG. 3. Thus, when the first heat conductive member 132 is not in contact with the first projecting portion 114, since the forcing member 150 has heat insulating properties, the heat of the first distal gripping member 124 is hardly transferred to other parts via the first heat conductive member 132.

Conversely, as shown in FIG. 3, as the gripping section 100 is gradually opened from its closed state, the first heat conductive member 132 is deformed while in contact with the forcing member 150. If the gripping section 100 is further opened after the switching portion, the first heat conductive member 132 is separated from the forcing member 150 and comes to be in contact with the first projecting portion 114.

The mechanism of the second heat conductive member 182 of the second jaw 160 is the same as that of the first heat conductive member 132 of the first jaw 110. In other words, when the gripping section 100 is further closed after the switching position, the second heat conductive member 182 is in contact with the forcing member 150, but is not in contact with the second projecting portion 164, as shown in FIG. 3. In this state, the heat of the second distal gripping member 174 is not transferred to other portions. On the other hand, when the gripping section 100 is further opened after the switching position, the second heat conductive member 182 is separated from the forcing member 150 and is in contact with the second projecting portion 164, as shown in FIG. 2. In this state, the heat of the second distal gripping member 174 is transferred and radiated to the second jaw main body 162 via the second heat conductive member 182.

The region from the closed state in which the first distal gripping member 124 as a first gripping member and the second distal gripping member 174 as a second gripping member are closed to the switching position is called the first region. The region from the switching position to the opened state is called the second region. At this time, in the first region, the first heat conductive member 132 brings the first distal gripping member 124 and the first jaw main body 112 as a heat radiating member into a non-thermally contacted state. On the other hand, in the second region, the first heat conductive member 132 brings the first distal gripping member 124 and the first jaw main body 112 into a thermally contacted state. Similarly, in the first region, the second heat conductive member 182 brings the second distal gripping member 174 and the second jaw main body 162 as a heat radiating member into a non-thermally contacted state. On the other hand, in the second region, the second heat conductive member 182 brings the second distal gripping member 174 and the second jaw main body 162 into a thermally contacted state. The forcing member 150 deforms the first heat conductive member 132 and the second heat conductive member 182 to function as a deformation member that changes the thermally contacted state between the first distal gripping member 124 and the first jaw main body 112 and the thermally contacted state between the second distal gripping member 174 and the second jaw main body 162.

According to the treatment tool 10 of the foregoing present embodiment, the first distal gripping member 124 and the second distal gripping member 174 are thermally insulated when treatment is performed while living tissue is being gripped by the gripping section 100, in other words, when the gripping section 100 is closed. Accordingly, the heat does not escape from the first distal gripping member 124 and the second distal gripping member 174 to other portions, and treatment is efficiently performed. In contrast, when the gripping section 100 releases living tissue, in other words, when the gripping section 100 is opened, the first distal gripping member 124 is thermally connected to the first jaw main body 112, and the second distal gripping member 174 is thermally connected to the second jaw main body 162. As a result, the heat of the first distal gripping member 124 and the second distal gripping member 174 is transferred to other members and to open space. Accordingly, during a period when treatment is not performed, the first distal gripping member 124 and the second distal gripping member 174 are immediately cooled down. At this time, even when the gripping section 100 is not completely opened, an excellent cooling effect can be achieved in multiple states in which the gripping section 100 is not closed. Thus, according to the treatment tool 10 of the present embodiment, efficient treatment and heat radiation can be achieved.

Modification of First Embodiment

Next, a modification of the first embodiment will be described. Herein, differences from the first embodiment will be described, and elements specified by the same reference numbers carry out the same operations, and a duplicate description of such elements will be omitted. The treatment tool 10 of the first embodiment is a treatment tool that performs treatment on living tissue as a target for treatment, using high-frequency electric power. In contrast, the treatment tool 10 according to the present modification is a treatment tool that performs treatment on living tissue which is a target for treatment, using energy of ultrasonic vibration.

FIG. 4 illustrates the outline of a configuration example of a gripping section 200 of the treatment tool 10 according to the present modification. As shown in FIG. 4, an ultrasonic vibration probe 260 is provided in the gripping section 200 of the present modification. The ultrasonic vibration probe 260 is connected to a non-illustrated ultrasonic transducer provided in the handle 12, through the shaft 16. The ultrasonic vibration probe 260 transmits ultrasonic vibration generated by the ultrasonic transducer, and vibrates. Although it vibrates, the ultrasonic vibration probe 260 does not change its position greatly with respect to the shaft 16.

A jaw 210 that changes its position so as to be opened and closed with respect to the ultrasonic vibration probe 260 is provided in the gripping section 200 of the present modification. The jaw 210 has a structure similar to that of the first jaw 110 of the first embodiment. In other words, the jaw 210 includes a jaw main body 212, a heat insulating member 222, a distal gripping member 224, and a heat conductive member 232. The jaw main body 212, the heat insulating member 222, the distal gripping member 224, and the heat conductive member 232 have the structures respectively similar to the structures of the first jaw main body 112, the first heat insulating member 122, the first distal gripping member 124, and the first heat conductive member 132 of the first embodiment.

A forcing member 250 is provided in the gripping section 200 of the present modification. The forcing member 250 is made of a heat insulating material. The forcing member 250 is designed to cover the outer periphery of the ultrasonic vibration probe 260. A part of the forcing member 250 projects in the direction of the jaw 210, penetrating the second hole 227 provided in the jaw main body 212 and coming out to the outside of the jaw main body 212.

The heat conductive member 232 connected to the distal gripping member 224 extends to the outside of the jaw main body 212 through the first hole 226 provided in the jaw main body 212. When the jaw 210 is closed with respect to the ultrasonic vibration probe 260, the heat conductive member 232 is in contact with the forcing member 250, and is not in contact with the projecting portion 214 of the jaw main body 212, as shown in FIG. 4. On the other hand, when the jaw 210 is opened with respect to the ultrasonic vibration probe 260, the heat conductive member 232 is in contact with the projecting portion 214 of the jaw main body 212, without being in contact with the forcing member 250.

In the gripping section 200 according to the present modification, the ultrasonic vibration probe 260 functions as a second distal gripping member. According to the gripping section 200 of the present modification, living tissue is gripped by the ultrasonic vibration probe 260 and the jaw 210. This living tissue is treated by frictional heat caused by the vibration of the ultrasonic vibration probe 260 and by heat generated by a high-frequency current flowing between the ultrasonic vibration probe 260 and the jaw 210.

According to the present modification, similar to the first embodiment, when treatment is performed, in other words, the jaw 210 is closed with respect to the ultrasonic vibration probe 260, the distal gripping member 224 is thermally insulated, and treatment is efficiently performed. On the other hand, when treatment is not performed, in other words, when the jaw 210 is opened with respect to the ultrasonic vibration probe 260, the distal gripping member 224 is cooled. Efficient treatment and cooling can be realized even by the treatment tool 10 according to the present modification.

An example of the treatment tool that performs treatment on living tissue using high-frequency electric power is presented in the first embodiment, and an example of the treatment tool that performs treatment on living tissue using high-frequency electric power and ultrasonic vibration is presented in the modification; however, a treatment tool is not limited thereto. The treatment tool 10 may use only ultrasonic vibration to perform treatment on living tissue. A heater may be provided in the gripping section 100, so that the treatment tool 10 performs treatment on living tissue using heat generated by the heater. The treatment tool 10 may perform treatment using one or more types of energy chosen from high-frequency electric power, ultrasonic vibration, heat generated by a heater, or any other form of energy.

The structure of the gripping section 100 is not limited to those shown in FIG. 2 to FIG. 4. Any structure may be adopted as long as the heat conductive member brings the first gripping member and the heat radiating member into a non-thermally contacted state in the first region and brings the first gripping member and the heat radiating member into a thermally contacted state in the second region in the process of changing from the state in which the first gripping member and the second gripping member are closed to the opened state. In the above-described embodiment, a case of switching between the two states by the deformation of the heat conductive member in the open/close direction of the gripping section 100 as the gripping section 100 is opened/closed is presented, as an example.

In the above-described first embodiment, an example of the first jaw 110 and the second jaw 160 constituting a symmetrical structure is presented; however, the structure of the gripping section 100 may be asymmetrical, as in the modification. When a heat conductive member brings a first gripping member and a heat radiating member into a non-thermally contacted state in the first region, and the heat conductive member brings the first gripping member and the heat radiating member into a thermally contacted state in the second region, one in a pair of the gripping members of the gripping section 100 that is cooled using the heat conductive member corresponds to the first gripping member.

Second Embodiment

The second embodiment of the present invention is described. Herein, differences from the first embodiment will be described, and elements specified by the same reference numbers carry out the same operations, and a duplicate description of such elements will be omitted. The treatment tool 11 according to the present embodiment has a shape as shown in FIG. 5, unlike the treatment tool 10 of the first embodiment. In the treatment tool 11 of the present embodiment, the mechanism of switching between the heat insulating state and the heat radiating state in the gripping section 300 is different from that of the first embodiment.

As shown in FIG. 5, the treatment tool 11 according to the present embodiment has a stationary handle 17 and a movable handle 18. When the movable handle 18 changes its position with respect to the stationary handle 17, the gripping section 300 in the distal portion of the treatment tool 11 is opened and closed. In the gripping section 300, the portion connected to the movable handle 18 is called the first jaw 310, and the portion connected to the stationary handle 17 is called the second jaw 380. In the treatment tool 11 of the present embodiment, switches 19 corresponding to the foot switch 30 of the first embodiment is arranged in the stationary handle 17.

Figure 6:
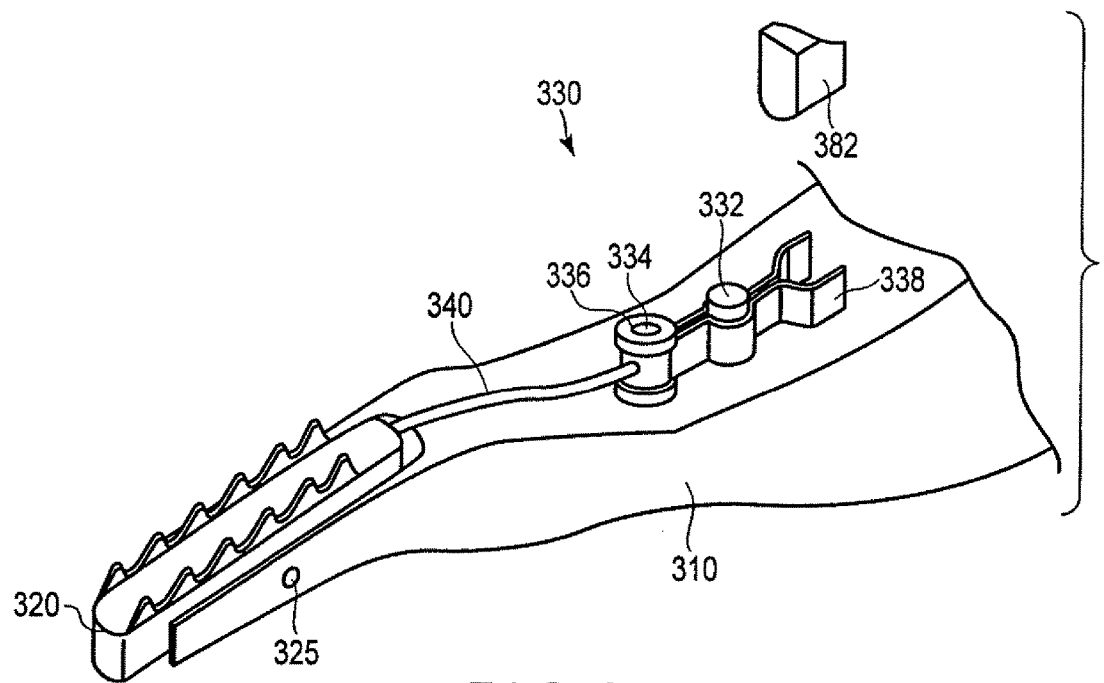
FIG. 6 is a perspective view showing an outline of a configuration example of a gripping section according to the second embodiment.

FIG. 6 is a perspective view of a structure around the first jaw 310 among the constituent elements of the gripping section 300 in the distal portion of the treatment tool 11. The first jaw 310 connected to the movable handle 18 is made of a metal, etc. having good heat conductivity, such as aluminum. The first jaw 310 is relatively large in volume and thus has a large heat capacity. The first jaw 310 has a large surface area and thus excels at heat radiating performance. In this manner, the first jaw 310 functions as a heat radiating member.

The distal portion of the first jaw 310 is connected to the distal gripping member 320. The distal gripping member 320 is made of a metal, such as stainless steel. The distal gripping member 320 is a portion that grips living tissue as a target for treatment. The distal gripping member 320 is supported by a support pin 325 connected to the first jaw 310, and is designed in such a manner that the angle with respect to the first jaw 310 changes. With such a configuration, the distal gripping member 320 can be in contact with living tissue in a large area size, regardless of a shape or an angle of living tissue. A space is provided between the first jaw 310 and the distal gripping member 320, and the first jaw 310 and the distal gripping member 320 are connected mainly by the support pin 325 only. The distal gripping member 320 is supplied with high-frequency electric power at, for example, the support pin 325.

Figure 7:
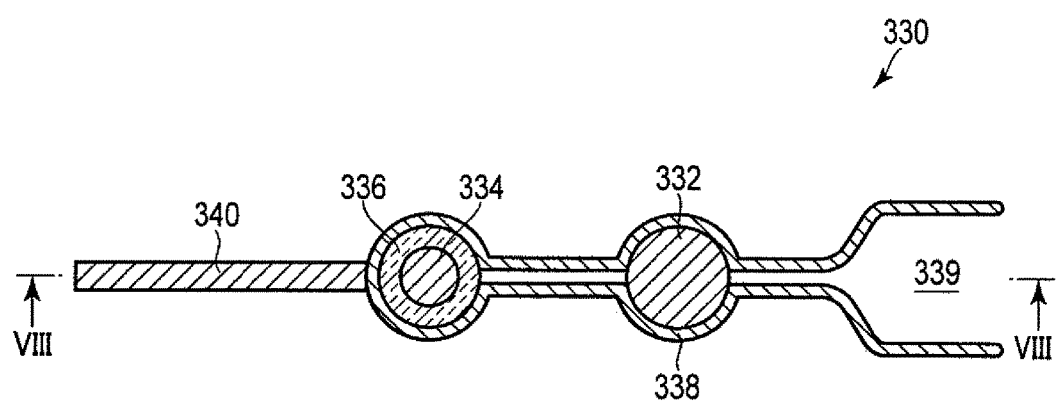
FIG. 7 is a cross-sectional view showing an outline of a configuration example of a heat transfer state switching mechanism according to the second embodiment, and showing an opened state of the gripping section.
Figure 8:
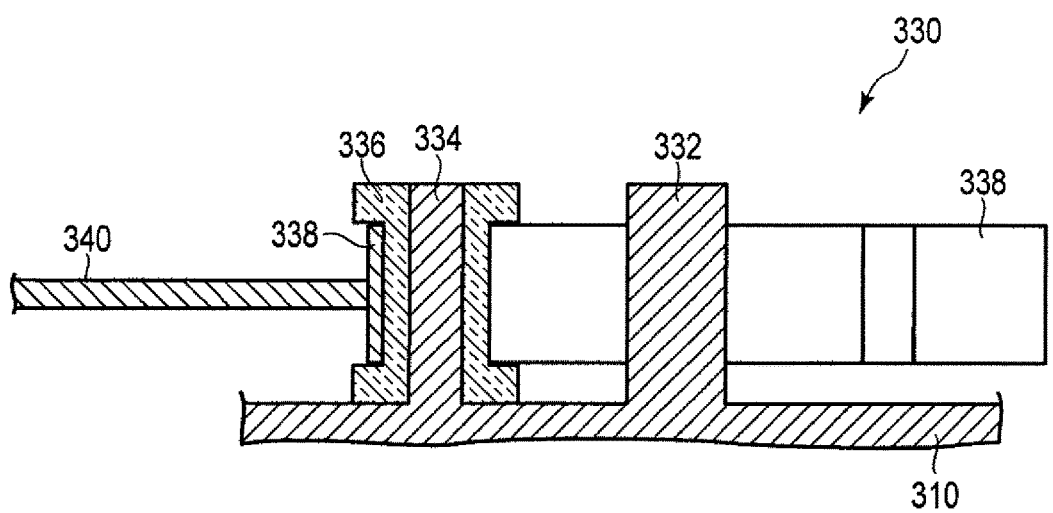
FIG. 8 is a cross-sectional view showing an outline of a configuration example of the heat transfer state switching mechanism according to the second embodiment.

A heat transfer state switching mechanism 330 is provided in a surface of the first jaw 310 that faces the second jaw 380. FIG. 7 shows a cross-sectional view of the heat transfer state switching mechanism 330 viewed from the second jaw 380. FIG. 8 shows a cross-sectional view taken from line VIII-VIII shown in FIG. 7.

As shown in these drawings, the heat transfer state switching mechanism 330 includes a first pillar portion 332 and a second pillar portion 334 projecting from the first jaw 310 in the direction of the second jaw 380. The first pillar portion 332 and the second pillar portion 334 are column-shaped and arranged in such a manner that their bottom surfaces are in contact with a surface of the first jaw 310 that faces the second jaw 380. The first pillar portion 332 and the second pillar portion 334 are formed integrally with the first jaw 310. The first pillar portion 332 is arranged on the proximal side of the second pillar portion 334. A heat insulating member 336 having approximately a cylindrical shape is provided on the circumferential surface of the second pillar portion 334.

The heat transfer state switching mechanism 330 includes a first heat conductive member 338 and a second heat conductive member 340. The first heat conductive member 338 consists of plate-shaped members having elasticity and a heat transfer capability. The first heat conductive member 338 is made of a metal plate, for example. As shown in FIG. 7, the first heat conductive member 338 is wound around the heat insulating member 336 that is around second pillar portion 334, and extends in the direction of the first pillar portion 332 from the proximal side of the heat insulating member 336 in such a manner that the two plates are arranged in parallel. Furthermore, the first heat conductive member 338 is arranged in such manner that the aforementioned two parallel plates are pressed against the periphery of the first pillar portion 332 halfway around the first pillar portion 332. Furthermore, the first heat conductive member 338 extends in the proximal direction in such a manner that the two plates are arranged in parallel from the proximal side of the first pillar portion 332. The first heat conductive member 338 is bent on its proximal side so as to form a space 339.

A second heat conductive member 340 is connected to the distal side of the first heat conductive member 338. The second heat conductive member 340 is made of a material having a high heat conductivity and flexibility. The second heat conductive member 340 is a wire, etc. made of a metal, such as a copper strand. One end of the second heat conductive member 340 is connected to the first heat conductive member 338 as aforementioned, and the other end of the second heat conductive member 340 is connected to the distal gripping member 320. Since the second heat conductive member 340 is flexible, it does not impede the movement of the distal gripping member 320.

As shown in FIG. 6 and FIG. 7, the first heat conductive member 338 and the first pillar portion 332 are in contact with each other when nothing is present in the space 339. Thus, the heat of the distal gripping member 320 is transferred to the first heat conductive member 338 via the second heat conductive member 340, further to the first pillar portion 332 via the first heat conductive member 338, i.e., to the first jaw 310, and is radiated into open space from the first jaw 310. Thus, the distal gripping member 320 is cooled down.

A projecting portion 382 is provided in a portion of the second jaw 380 that faces the space 339 of the first heat conductive member 338. The projecting portion 382 is made of a heat-insulating material. The projecting portion 382 is designed to be inserted into the space 339 when the first jaw 310 and the second jaw 380 are further closed after a predetermined position. The width of the projecting portion 382 is wider than the width of the gap between the two opposing plates of the first heat conductive member 338 in the space 339.

Figure 9:
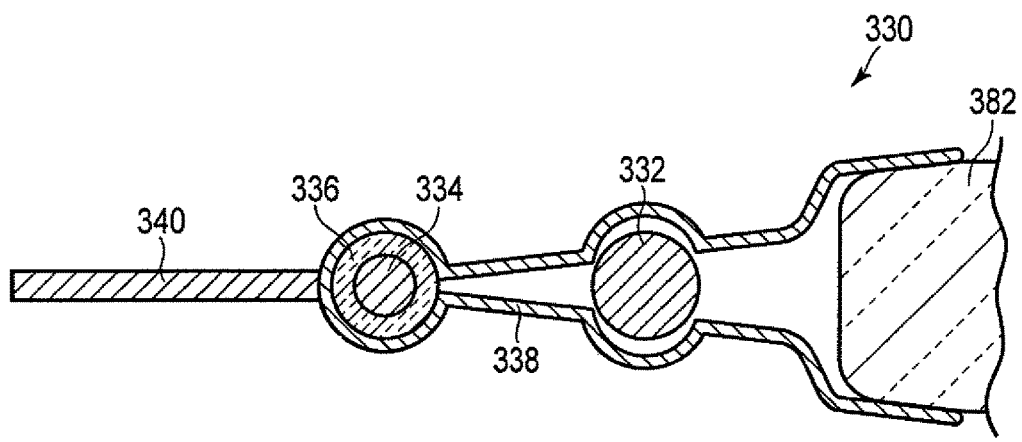
FIG. 9 is a cross-sectional view showing an outline of a configuration example of the heat transfer state switching mechanism according to the second embodiment, and showing a closed state of the gripping section.

Accordingly, when the first jaw 310 and the second jaw 380 are closed, the projecting portion 382 is inserted into the space 339, and as shown in FIG. 9, the first heat conductive member 338 spreads apart. As a result, a space emerges between the first heat conductive member 338 and the first pillar portion 332, and the contacted state is eliminated. At this time, the first heat conductive member 338 and the second heat conductive member 340 connected to the distal gripping member 320 are in contact only with the heat insulating member 336 having heat insulating properties and the projecting portion 382 of the second jaw 380 having heat insulating properties; thus, the distal gripping member 320 is not cooled down.

A position of the first jaw 310 and the second jaw 380 when the first heat conductive member 338 not in contact with the first pillar portion 332 is switched to a contacted state will be called a switching position. The region from the closed state in which the distal gripping member 320 as a first gripping member and the second jaw 380 as a second gripping member are closed to the switching position is called the first region, and the region from the switching position to the opened state is called the second region. At this time, in the first region, the first heat conductive member 338 and the second heat conductive member 340 bring the distal gripping member 320 and the first jaw 310 as a heat radiating member into a non-thermally contacted state. In the second region, the first heat conductive member 338 and the second heat conductive member 340 bring the distal gripping member 320 and the first jaw 310 into a thermally contacted state. The projecting portion 382 functions as a deformation member that deforms the first heat conductive member 338 to change the thermally contacted state between the distal gripping member and the first jaw 310.

According to the treatment tool 11 of the present embodiment, when treatment is performed while living tissue is being gripped by the gripping section 300, in other words, when the gripping section 300 is closed, the distal gripping member 320 is thermally insulated and the treatment is efficiently performed. In contrast, when the gripping section 300 releases the living tissue, in other words, when the gripping section 300 is opened, the distal gripping member 320 is thermally connected to the first jaw 310, and the heat of the distal gripping member 320 is transferred to other members or to open space; thus, the distal gripping member 320 is immediately cooled down. At this time, even when the gripping section 300 is not completely opened, the cooling effect can be achieved in multiple states in which the gripping section 300 is not closed. Thus, according to the treatment tool 11 of the present embodiment, efficient treatment and heat radiation can be achieved.

According to the present embodiment, the heat transfer state switching mechanism 330 is provided on a side where the first jaw 310 faces the second jaw 380, i.e., the inner side. Accordingly, in comparison to a treatment tool not having the heat transfer state switching mechanism 330, an outer shape or an outer dimension in the first jaw 310 and the second jaw 380 in a closed state are almost unchanged.

A heat transfer mechanism similar to that provided in the first jaw 310 may also be provided in the second jaw 380. The treatment tool 11 may be a treatment tool using high-frequency electric power, or one using ultrasonic vibration, or one using heat generated by a heater, or any combinations thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool comprising:
   a first gripping member;
   a second gripping member configured to be opened and closed with respect to the first gripping member;
   a heat radiating member;
   a first heat conductive member that is connected to the first gripping member; and
   a first projecting portion that is located between the heat radiating member and the first heat conductive member, wherein:
   in a first, open state, the first projecting portion is in contact with the first heat conductive member so that the first gripping member and the heat radiating member are thermally connected by the first heat conductive member,
   in a second, closed state, the first projecting portion is not in contact with the first heat conductive member so that the first gripping member and the heat radiating member are not thermally connected by the first heat conductive member, and
   in a switching state, during which the treatment tool transitions from the second, closed state to the first, open state, the first gripping member and the heat radiating member are not thermally connected by the first heat conductive member until the treatment tool assumes the first, open state.

2. The treatment tool according to claim 1, wherein the first heat conductive member includes an elastic member having a heat transfer capability.

3. The treatment tool according to claim 2, further comprising a deformation member that is configured to deform the first heat conductive member so that the treatment tool assumes the second, closed state.

4. The treatment tool according to claim 3, wherein the deformation member is a heat insulating member that physically contacts the first heat conductive member to deform that first heat conductive member.

5. The treatment tool according to claim 3, wherein the deformation member is a heat insulating member.

6. The treatment tool according to claim 5, wherein
   the first heat conductive member is provided in the first gripping member, and
   the deformation member is provided in the second gripping member.

7. The treatment tool according to claim 1, wherein the first heat conductive member is a flexible member.

8. The treatment tool according to claim 1, further comprising a second heat conductive member such that:
   in the first, open state, the second gripping member and the heat radiating member are thermally connected by the second heat conductive member,
   in the second, closed state, the second gripping member and the heat radiating member are not thermally connected by the second heat conductive member, and
   in the switching state, the second gripping member and the heat radiating member are not thermally connected by the second heat conductive member until the treatment tool assumes the first, open state.

9. The treatment tool according to claim 1, wherein:
   in the first, open state, heat from the first gripping member is transferred to the heat radiating member, and
   in the second, closed state, heat from the first gripping member is not transferred to the heat radiating member.

10. The treatment tool according to claim 1, wherein the first gripping member is an electrode.

11. The treatment tool according to claim 1, wherein the first heat conductive member is fixed to the first gripping member during the first, open state and during the second, closed state.

* * * * *